US010948388B2

(12) United States Patent
Yamasaki et al.

(10) Patent No.: US 10,948,388 B2
(45) Date of Patent: Mar. 16, 2021

(54) SMEAR PREPARATION APPARATUS, BLOOD SAMPLE PROCESSING SYSTEM, AND METHOD OF WASHING BLOOD PROCESSING UNIT OF THE SMEAR PREPARATION APPARATUS

(71) Applicant: Sysmex Corporation, Kobe (JP)

(72) Inventors: Mitsuo Yamasaki, Kobe (JP); Seiya Shinabe, Kobe (JP); Akio Toyoda, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 15/196,705

(22) Filed: Jun. 29, 2016

(65) Prior Publication Data

US 2017/0003204 A1  Jan. 5, 2017

(30) Foreign Application Priority Data

Jun. 30, 2015 (JP) .................................. 2015-132111

(51) Int. Cl.
G01N 1/28 (2006.01)
B08B 3/08 (2006.01)
G01N 33/80 (2006.01)
G01N 35/10 (2006.01)
G01N 35/00 (2006.01)

(52) U.S. Cl.
CPC ............ *G01N 1/2813* (2013.01); *B08B 3/08* (2013.01); *G01N 33/80* (2013.01); *G01N 35/00029* (2013.01); *G01N 35/1004* (2013.01)

(58) Field of Classification Search
None
See application file for complete search history.

(56) References Cited

U.S. PATENT DOCUMENTS

| 6,114,292 | A | 9/2000 | Hoshiko et al. |
| 6,428,752 | B1 | 8/2002 | Montagu |
| 9,217,750 | B2 | 12/2015 | Shibata et al. |
| 2003/0003022 | A1* | 1/2003 | Tamura ................ G01N 1/2813 422/519 |
| 2005/0161402 | A1 | 7/2005 | Hanafusa et al. |
| 2010/0108101 | A1 | 5/2010 | Shibata et al. |
| 2011/0054807 | A1 | 3/2011 | Mizumoto et al. |

(Continued)

FOREIGN PATENT DOCUMENTS

| CN | 1648670 A | 8/2005 |
| CN | 201692959 U | 1/2011 |

(Continued)

OTHER PUBLICATIONS

Chinese Office Action dated Apr. 25, 2019 in a counterpart Chinese patent application No. 201610195886.9.

(Continued)

*Primary Examiner* — Kathryn Wright
(74) *Attorney, Agent, or Firm* — Brinks Gilson & Lione

(57) ABSTRACT

A smear preparation apparatus comprises a blood processing unit, a washing unit, a controller, an information obtaining unit. The controller changes the washing condition for washing after processing a blood sample to a second washing condition which is stronger than the first washing condition when abnormal blood cells occur in the blood sample.

19 Claims, 7 Drawing Sheets

(56) References Cited

U.S. PATENT DOCUMENTS

| | | | | |
|---|---|---|---|---|
| 2012/0003731 A1* | 1/2012 | Kuroda | ............ | G01N 35/00732 435/288.7 |
| 2013/0260412 A1* | 10/2013 | Tatsutani | ................. | G01N 1/28 435/34 |
| 2013/0260415 A1 | 10/2013 | Fukuda et al. | | |
| 2014/0212344 A1 | 7/2014 | Nagaoka et al. | | |

FOREIGN PATENT DOCUMENTS

| | | |
|---|---|---|
| CN | 102348988 A | 2/2012 |
| CN | 103364573 A | 10/2013 |
| CN | 103733072 A | 4/2014 |
| JP | H10-96688 A | 4/1998 |
| JP | 2001-091523 A | 4/2001 |
| JP | 2008-202945 A | 9/2008 |
| JP | 2010-107398 | 5/2010 |
| JP | 2010-216876 | 9/2010 |
| JP | 2011-220928 A | 11/2011 |
| JP | 2011-247778 A | 12/2011 |
| JP | 2013-210249 | 10/2013 |
| JP | 2013-210266 A | 10/2013 |

OTHER PUBLICATIONS

Liu Sheimin et al., "Animal Pathology Physiology", Heilongjiang Educational Publishing Co.,Ltd., Jun. 2007, pp. 120-122; Cited in the Chinese Decision of Rejection dated Sep. 18, 2019 in a counterpart Chinese patent application No. 201610195886.9.

Chinese Decision of Rejection dated Sep. 18, 2019 in a counterpart Chinese patent application No. 201610195886.9.

Office Action, including English translation, in China Application No. 201610195886.9, dated Dec. 31, 2020, 24 pages.

* cited by examiner

SMEAR PREPARATION APPARATUS, BLOOD SAMPLE PROCESSING SYSTEM, AND METHOD OF WASHING BLOOD PROCESSING UNIT OF THE SMEAR PREPARATION APPARATUS

CROSS REFERENCE TO RELATED APPLICATIONS

This application claims priority from prior Japanese Patent Application No. 2015-132111, filed on Jun. 30, 2015, entitled "SMEAR PREPARATION APPARATUS, BLOOD SAMPLE PROCESSING SYSTEM, AND METHOD OF WASHING BLOOD PROCESSING UNIT OF THE SMEAR PREPARATION APPARATUS", the entire contents of which are incorporated herein by reference.

FIELD OF THE INVENTION

The present invention relates to a smear preparation apparatus, blood sample processing system, and method of washing the blood processing unit of the smear preparation apparatus.

BACKGROUND

Japanese Patent Application Publication No. 2011-247778 discloses a specimen processing apparatus which examines and analyzes blood. The specimen processing apparatus is provided with a measuring unit for analyzing blood, and a smear preparation apparatus for preparing smears. The smear preparation apparatus disclosed in patent document 1 automatically prepares a smear by processing a sample within a container.

SUMMARY OF THE INVENTION

The scope of the present invention is defined solely by the appended claims, and is not affected to any degree by the statements within this summary.

The smear preparation apparatus must wash the blood processing unit used to process the sample between the processing of each sample to prevent carryover in which the prior sample contaminates the smear currently being prepared. The prepared smear is used for microscopic clinical examination by a physician or the like based on the number, type, and morphology of cells contained in the smear. For example, when cells not usually contained in the peripheral blood of healthy subjects, such as blasts contained in samples collected from patients with acute myeloid leukemia, are carried over to the next smear, there is a possibility of it adversely affecting accurate diagnosis by the clinical physician because acute myeloid leukemia is suggested by the presence of the blasts. Although the washing performed between the processing of each sample must be done adequately, the same washing operation is uniformly performed for samples of healthy subjects and samples of patients with, for example, acute myeloid leukemia, thereby increasing the time required for washing and reducing the processing power of the smear preparation apparatus. Moreover, there is concern of wasting the washing reagent due to excessive washing operations.

The invention reduces the impact of carryover on a smear, and improves processing performance of the smear preparation apparatus while reducing reagent consumption.

A first aspect of the invention is a smear preparation apparatus including a blood processing unit configured to process a blood sample and prepares a smear of the blood sample, a washing unit configured to wash the blood processing unit under a first washing condition after processing of the blood sample, a controller configured to control the operations of the blood processing unit and the washing unit, an information obtaining unit configured to obtain information relating to the occurrence of abnormal blood cells in a blood sample from an external source, wherein the controller is configured to change the washing condition for washing after processing a blood sample to a second washing condition which is stronger than the first washing condition when abnormal blood cells occur in the blood sample.

A second aspect of the invention is a blood sample processing system including a blood cell analyzer configured to analyzes blood cells in a blood sample, and a smear preparation apparatus including a blood processing unit configured to prepare a smear of a blood sample by processing the blood sample, a washing unit configured to wash the blood processing unit, and a controller configured to control the operations of the blood processing unit and the washing unit, wherein the blood cell analyzer is configures to generate wash condition change order information which changes the washing operation of the smear preparation apparatus to a second washing condition that is stronger than the first washing condition, the smear preparation apparatus comprises an information obtaining unit configured to obtain the washing condition change order information from the blood cell analyzer, and the controller of the smear preparation apparatus is configured to change the washing performed after processing of a blood sample to a second washing condition that is stronger than the first washing condition based on the washing condition change order information obtained from the blood cell analyzer by the information obtaining unit.

A third aspect of the invention is a method of washing a blood processing unit of a smear preparation apparatus including a blood processing unit configured to prepare a smear of a blood sample by processing the blood sample, and a washing unit configured to wash the blood processing unit under a first washing condition after processing the blood sample, the method comprising performing washing after processing a blood sample under a second washing condition that is stronger than the first washing condition when information related to the presence of abnormal blood cells in a blood sample being used to prepare a smear is obtained from an external source.

DETAILED DESCRIPTION OF THE PREFERRED EMBODIMENT

The embodiment is described below based on the drawings.

The structure of the smear preparation apparatus 30 of the embodiment is described referring to FIGS. 1 through 7.

Figure 1:
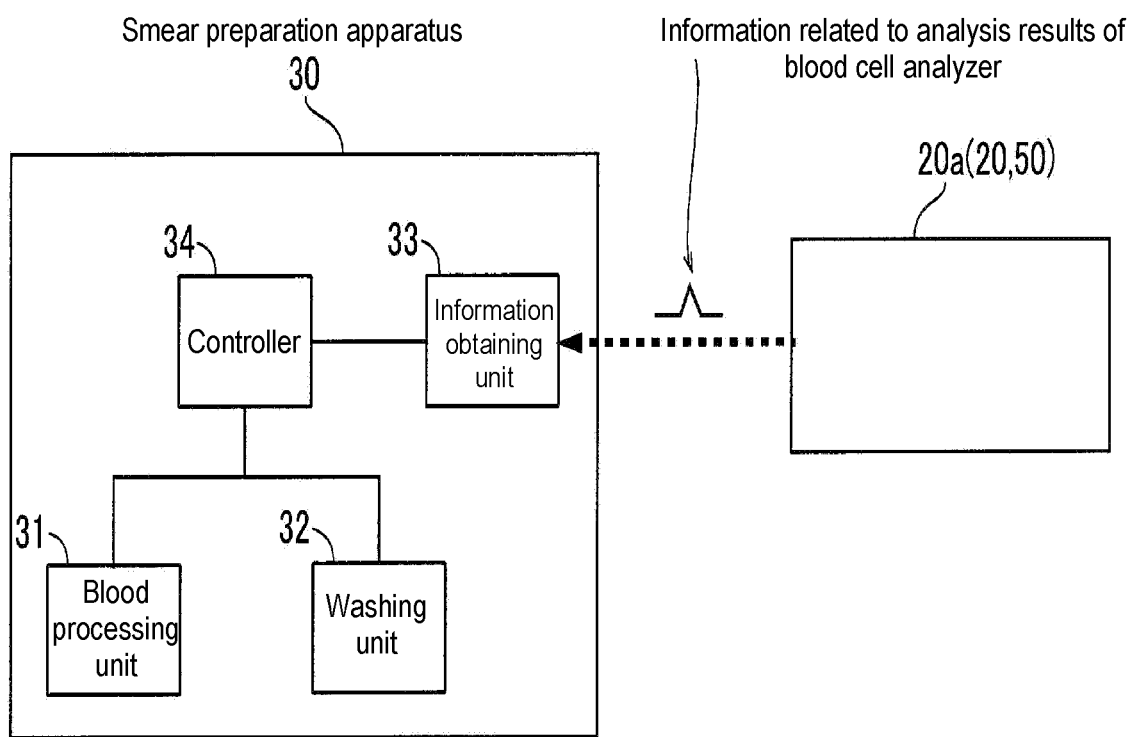
FIG. 1 is a schematic view briefly showing an embodiment of the blood sample processing system.

As shown in FIG. 1, the smear preparation apparatus 30 has a blood processing unit 31, washing unit 32, information obtaining unit 33, and controller 34. The smear preparation apparatus 30 is a device which prepares slide samples from blood samples. The smear preparation apparatus 30, for example, prepares a smear of a blood sample when an order to prepare a smear is received, and when an external device 20a determines it is necessary to prepare a smear. A smear is prepared by spreading a blood sample on a glass slide to observe the blood cells. The blood sample on the smear also may undergo a staining process by a well know staining liquid, although a staining process is not required.

The blood processing unit 31 is provided to process the blood sample to prepare the smear of the blood sample. The blood processing unit 31 processes the blood sample to prepare the smear The washing unit 32 is provided to wash the blood processing unit 31. The washing unit 32 can wash the blood processing unit 31 under a first washing condition after processing a blood sample. The first washing condition represents the normal washing condition. The washing unit 32 can wash the blood processing unit 31 under a second washing condition which is a stronger washing condition than the first washing condition after processing the blood sample.

The information obtaining unit 33 can obtain information from an external source. The information obtaining unit 33 obtains information relating to the presence of abnormal blood cells in the blood sample from an external device 20a. The external device 20a, for example, also may be the blood cell analyzer 20 or a host computer 50 or the like. The information obtaining unit 33, for example, is an interface part for the input and output of signals. According to this configuration, for example, the controller 34 can readily obtain information relating to the presence of abnormal blood cells through the information obtaining unit 33.

The controller 34 includes a CPU. The controller 34 is provided to control the operations of the blood processing unit 31 and the washing unit 32. The controller 34 can obtain information from the information obtaining unit 33. The controller 34 changes the washing condition for washing after processing a blood sample to the second washing condition which is stronger than the first washing condition when abnormal blood cells occur in the blood sample. The controller 34 controls the operation of the washing unit 32 under the second washing condition when abnormal blood cells are present in the blood sample.

For example, the controller 34 obtains information relating to the number of abnormal blood cells as the information related to the occurrence of abnormal blood cells in the blood sample, and changes the washing condition for washing after processing of the blood sample to the second washing condition that is stronger than the first washing condition based on the obtained information. The information relating to the number of abnormal blood cells also may be the number of abnormal blood cells itself.

For another example, the controller 34 obtains the abnormal blood cell flag as the information related to the occurrence of abnormal blood cells in the blood sample, and changes the washing condition for washing after processing of the blood sample to the second washing condition that is stronger than the first washing condition.

According to the above configuration, the washing operation is changed from the first washing condition to the second washing condition that is stronger than the first washing condition when a blood sample containing blood cells that may influence the diagnosis is processed by the blood processing unit 31 even when only slightly present as in the case of blood cells not normally found in peripheral blood of healthy subjects such as blasts in a sample from a patient with acute myeloid leukemia. Therefore, carryover of abnormal blood cells that would adversely influence diagnosis with even a slight presence can be effectively prevented and the processing power of the smear preparation apparatus 30 is improved. The time required to prepare the smear also is prevented from increasing and consumption of reagent such as washing liquid is also limited compared to performing the strong washing operation every time, for example, the same as washing after processing a sample of a patient with acute myeloid leukemia even when the sample is that of a healthy subject. Accordingly, the impact of carryover on a smear is prevented, and the processing power of the smear preparation apparatus 30 is improved while reducing reagent consumption.

The structure of the preferred embodiment of the smear preparation apparatus 30 shown in FIG. 1 is described in detail below referring to FIG. 2 and subsequent drawings.

Figure 2:
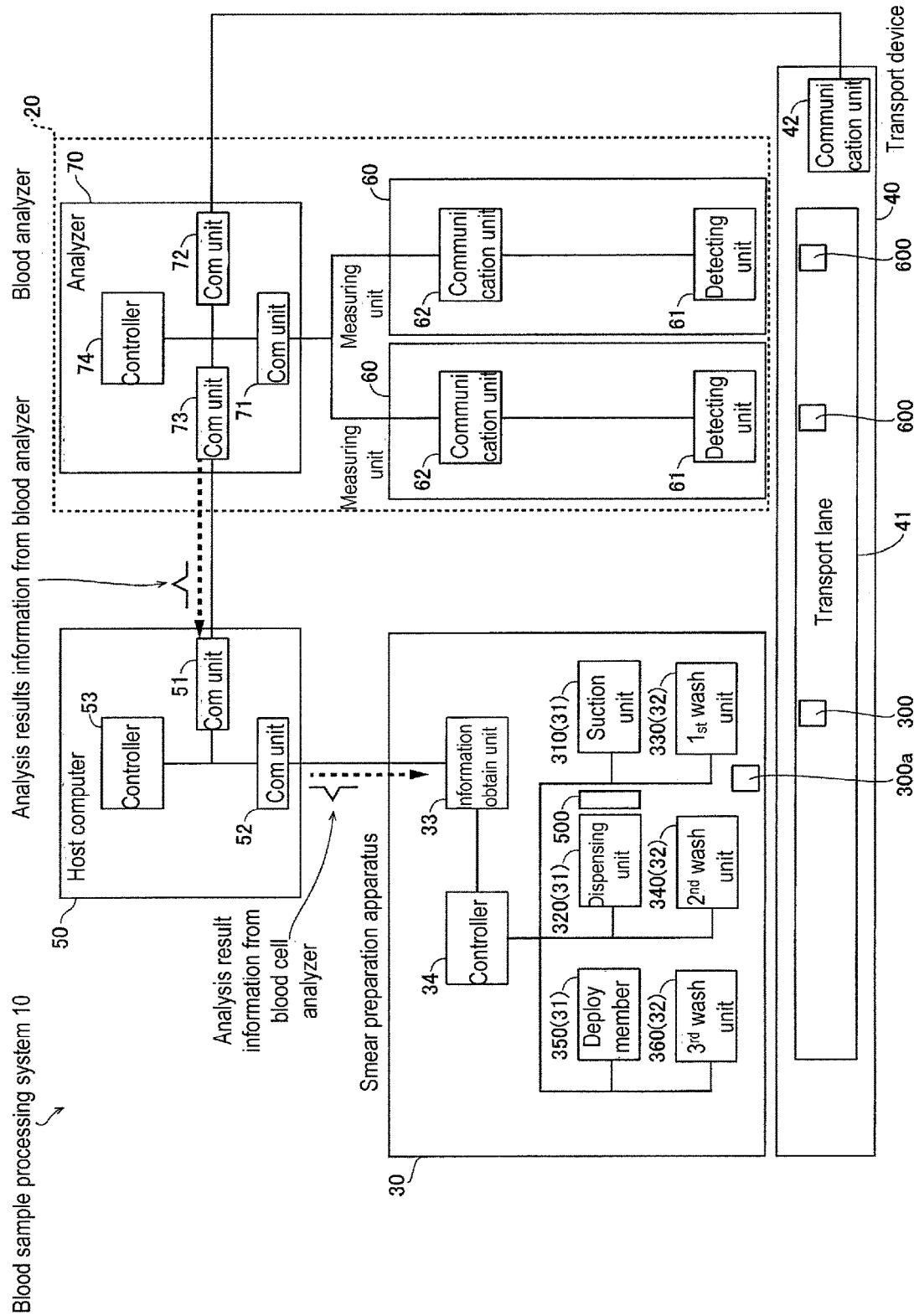
FIG. 2 is a block diagram of the embodiment of the blood sample processing system.

As shown in FIG. 2, the smear preparation apparatus 30 is incorporated in, for example, a blood sample processing system 10 together with a blood cell analyzer 20. The blood sample processing system 10 may also include a transporting unit 40 and host computer 50 in addition to the blood cell analyzer 20 and smear preparation apparatus 30. For the convenience of description, the transporting unit 40 and host computer 50 are described first, followed by descriptions of the blood cell analyzer 20 and smear preparation apparatus 30.

The transport unit 40 transports test tubes containing blood samples. The transport unit 40 has a transport lane 41, and communication unit 42. The transport unit 40 is capable of transporting the test tube containing a blood sample on the transport lane 41. The communication unit 42 is, for example, an interface part for the input and output of signals.

The host computer 50 is installed in a facility such as a hospital, laboratory or the like to perform integrated management of measurement order issued to a plurality of blood cell analyzers installed in the facility, and analysis results obtained by analysis of samples by the blood cell analyzers pursuant to the measurement orders. The host computer 50 also is connected to the plurality of blood cell analyzers installed in the facility, and manages the progress of the clinical examination operations within the facility. The host computer 50 has communication units 51 and 52, and a controller 53. The controller 53 includes a CPU. The host computer 50 is, for example, a LIS (Laboratory Information System) that receives measurement orders input by operators and transmitted from other devices such as an electronic health record system, and stores and manages the received orders. The host computer 50 receives the order request from the blood cell analyzer 20, and transmits the requested order to the blood cell analyzer 20. The host computer 50 receives analysis results such as blood cell type and blood cell count and the like from the blood cell analyzer 20, and stores and manages the information related to the analysis results. The host computer 50 also is connected to the smear preparation apparatus 30 and the blood cell analyzer 20 in a manner allowing communication to manage the progress of the smear preparation of the smear preparation apparatus 30 and the progress of the analysis of the blood cell analyzer 20.

Blood Analyzer Structure

The blood cell analyzer 20 is arranged externally to the smear preparation apparatus 30. The blood cell analyzer 20 is provided to analyze the blood cells in the blood sample. The blood cell analyzer 20 is, for example, multi-function blood cell analyzer. Specifically, the blood cell analyzer 20 is a blood cell counter which classifies and counts the blood cells in the blood sample. The blood cell analyzer 20 determines whether to have the smear preparation apparatus 30 prepare a smear based on the results of the analysis of the blood cells in the blood sample.

The blood cell analyzer 20 includes a measuring unit 60 and an analyzing unit 70.

The measuring unit 60 is provided to measure blood samples. The measuring unit 60 includes a detecting unit 61 and a communication unit 62. The measuring unit 60 is connected to the analyzing unit 70 through the communication unit 62. The communication unit 62 is, for example, an interface part for the input and output of signals. Note that although two measuring units 60 are shown in the example in FIG. 2, the number of installed measuring units 60 may be changed as appropriate. The measuring units 60 may be devices of identical specifications or devices of different specifications.

The detecting unit 61 measures the blood sample transported to the suction process position 600 by the transporting unit 40. The detecting unit 61 detects red blood cells (RBC detection) and detects platelets (PLT detection) by a sheath flow DC detection method. The detecting unit 61 detects hemoglobin (HGB detection) in the blood by the SLS-hemoglobin method. The detecting unit 61 detects white blood cells (WBC detection) by flow cytometric method using a semiconductor laser. The measurement data obtained by the detecting unit 61 is sent to the analyzing unit 70 through the communication unit 62.

The analyzing unit 70 includes communication units 71 through 73, and controller 74. The controller 74 includes a CPU. The analyzing unit 70 and the measuring unit 60 are connected to the communication unit 71 and the communication unit 62 and are mutually capable of sending and receiving information. The communication unit 71 is connected to each communication unit 62 in the two measuring units 60. The analyzing unit 70 and the transporting unit 40 are connected to the communication unit 72 and the communication unit 42 and are mutually capable of sending and receiving information. The analyzing unit 70 and the host computer 50 are connected to the communication unit 73 and the communication unit 51 and are mutually capable of sending and receiving information.

The analyzing unit 70 can be connected to a plurality of blood cell analyzers 20, and can control the operation of the plurality of blood cell analyzers 20. The analyzing unit 70 also classifies blood cells contained in the sample based on the scattered light intensity and fluorescent light intensity of the blood cells in the sample which is obtained by the measuring unit 60, then counts the number of blood cells of every type. For example, the analyzing unit 70 counts the number of normal white blood cells, the number of normal red blood cells, and the number of abnormal blood cells.

Abnormal blood cells are blood cells which are not usually found in the peripheral blood of healthy subjects, for example abnormal red blood cells and abnormal white blood cells. Abnormal white blood cells include, for example, juvenile, atypical lymphocytes, and plasma cells. The concept of immature blood cells includes promyelocytes, myelocytes, metamyelocytes, and blasts. Abnormal red blood cells include, for example, nucleated red blood cells and sickle cells.

The analyzing unit 70 controls the transporting unit 40. The analyzing unit 70 sends signals for the operation of the transporting unit 40 to the transporting unit 40 to transport a test tube containing a blood sample to the suction process position 300 where the suction process is performed on the sample by the smear preparation apparatus 30 and the suction process position 600 where a suction process is performed on the sample by the measuring unit 60.

The analyzing unit 70 is provided to receive the measurement data from the measuring unit 60 and analyze the blood sample. Specifically, the controller 74 of the analyzing unit 70 analyzes the normal white blood cell count, the normal red blood cell count, the abnormal white blood cell count, or the abnormal red blood cell count of the blood sample using a provided program based on the measurement data obtained from the measuring unit 60. The analyzing unit 70 also determines whether the normal white blood cell count, the normal red blood cell count, the abnormal white blood cell count, or the abnormal red blood cell count of the blood sample exceeds set threshold values corresponding to the normal white blood cell count, the normal red blood cell count, the abnormal white blood cell count, or the abnormal red blood cell count based on the measurement data obtained from the measuring unit 60. Note that in the specification "white blood cell count" refers to the normal white blood cell count, and "red blood cell count" refers to the normal red blood cell count.

The controller 74 of the analyzing unit 70 sets the abnormal white blood cell count threshold value and the abnormal red blood cell count threshold value at, for example, zero [0]. Therefore, the controller 74 can analyze the presence or absence of abnormal white blood cells and abnormal red blood cells based on the measurement results received from the measuring unit 60. The controller 74 of the analyzing unit 70 also counts the number of white blood cells and the number of red blood cells based on the measurement results received from the measuring unit 60. The controller 74 also obtains information relating to, for example, hematocrit, platelet count, and hemoglobin in the blood sample based on the measurement results received from the measuring unit 60.

The blood cell analyzer 20 as a device external to the smear preparation apparatus 30 generates information relating to the presence of abnormal blood cells. Specifically, the controller 74 of the analyzing unit 70 generates information relating to the presence of abnormal blood cells.

For example, the controller 74 also may generate the number of abnormal blood cells as the information relating to the presence of abnormal blood cells based on the results of the analysis of the blood cells of the blood sample.

The controller 74 also may generate information suggesting the presence of abnormal blood cells as the information relating to the presence of abnormal blood cells based on the results of the analysis of the blood cells of the blood sample. For example, the controller 74 also may generate an abnormal blood cell flag as the information suggesting the presence of abnormal blood cells. Specifically, the controller 74 may generate the abnormal blood cell flag when at least one among the white blood cell count, red blood cell count, abnormal white blood cell count, or abnormal red blood cell count in the analysis results of the blood cell analyzer 20 is greater than the set threshold value corresponding to the white blood cell count, red blood cell count, abnormal white blood cell count, or abnormal red blood cell count.

The controller 74 also may generate wash condition change order information to change the washing operation of the smear preparation apparatus 40 from the first washing operation to the second washing operation based on the contained information related to the presence of abnormal blood cells in the analysis results of the blood sample. Specifically, the controller 74 generates the wash condition change order information when at least one among the white blood cell count, red blood cell count, abnormal white blood cell count, or abnormal red blood cell count in the analysis results of the blood cell analyzer 20 is greater than the set threshold value corresponding to the white blood cell count, red blood cell count, abnormal white blood cell count, or abnormal red blood cell count.

The wash condition change order information or information related to the presence of abnormal blood cells is sent from the analyzing unit 70 to the smear preparation apparatus 30.

The host computer 50 also may generate wash condition change order information. Specifically, the host computer 50 stores the information on the thresholds of the white blood cell count, red blood cell count, abnormal white blood cell count, or abnormal red blood cell count, and obtains the white blood cell count, red blood cell count, abnormal white blood cell count, or abnormal red blood cell count from the blood cell analyzer 20. Then, the host computer 50 generates the wash condition change order information when at least one among the white blood cell count, red blood cell count, abnormal white blood cell count, or abnormal red blood cell count is greater than the set threshold value corresponding to the white blood cell count, red blood cell count, abnormal white blood cell count, and abnormal red blood cell count. The host computer 50 also can change and set the threshold values corresponding to the white blood cell count, red blood cell count, abnormal white blood cell count, or abnormal red blood cell count.

The washing condition also can be changed without using the wash condition change order information. For example, the controller 34 of the smear preparation apparatus 30 may obtain the abnormal blood cell flag as information suggesting the presence of abnormal blood cells generated by the blood cell analyzer 20 from the blood cell analyzer 20 through the host computer 50. The controller 34 of the smear preparation apparatus 30 also may obtain the abnormal blood cell flag as information suggesting the presence of abnormal blood cells generated by the host computer 50 from the host computer 50. The controller 34 then changes the washing condition from the first washing condition to the second washing condition based on the abnormal blood cell flag.

The controller 34 of the smear preparation apparatus 30 also stores the information on the thresholds of the white blood cell count, red blood cell count, abnormal white blood cell count, or abnormal red blood cell count, and obtains the white blood cell count, red blood cell count, abnormal white blood cell count, or abnormal red blood cell count from the analysis results of the blood cell analyzer 20 through the host computer 50. Then, the controller 34 may change the washing condition from the first washing condition to the second washing condition when at least one among the white blood cell count, red blood cell count, abnormal white blood cell count, or abnormal red blood cell count is greater than the set threshold value corresponding to the white blood cell count, red blood cell count, abnormal white blood cell count, and abnormal red blood cell count. The controller 34 also can change and set the threshold values corresponding to the white blood cell count, red blood cell count, abnormal white blood cell count, or abnormal red blood cell count.

The analyzing unit 70 can change and set the threshold values corresponding to blood cell count of at least one among the white blood cell count, red blood cell count, abnormal white blood cell count, or abnormal red blood cell count. Specifically, the controller 74 of the analyzing unit 70 and individually change and set the threshold values of at least one among the blood cell counts. Therefore, the condition for changing the washing condition of the washing operation can be set at a suitable numerical value.

Although a single blood cell analyzer 20 is installed in the example shown in FIG. 2, the number of installed blood cell analyzers 20 may be changed as appropriate.

Smear Preparation Apparatus Structure

The smear preparation apparatus 30 also may include a suction unit 310 and dispensing unit 320 as blood processing units 31, and first washing unit 330 and second washing unit 340 as washing units 32.

The information obtaining unit 33 is connected to the communication unit 52 and is capable of sending and receiving information with the host computer 50 and smear preparation apparatus 30.

Figure 3:
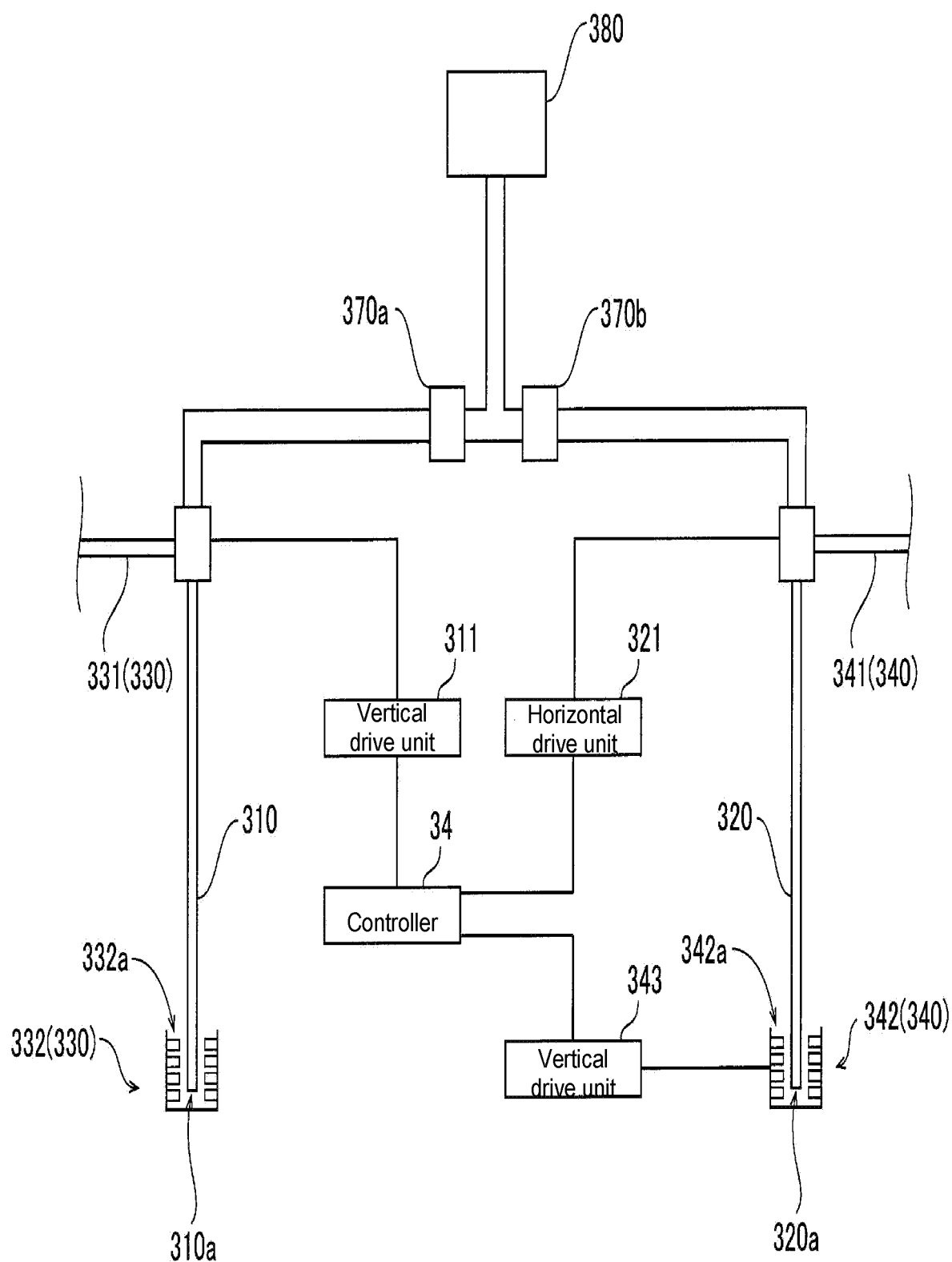
FIG. 3 is a schematic view showing the suction unit, dispensing unit, first washing unit, and second washing unit of the blood sample processing system of the embodiment.

As shown in FIG. 3, the suction unit 310 and dispensing unit 320 are connected to a pump 380. The pump 380 is, for example, a syringe pump. A valve 370a is provided between the suction unit 310 and the pump 380 to open and close the flow path. A valve 370b is provided between the dispensing unit 320 and the pump 380 to open and close the flow path. The valve 370a and the valve 370b open and close independently. Note that FIG. 3 shows the suction unit 310 and the dispensing unit 320 respectively being cleaned by the first washing unit 330 and the second washing unit 340.

The suction unit 310 is provided to suction blood from the test tube transported from the suction process position 300 to the smear preparation apparatus 30 side by a hand tool which is not shown in the drawing. The suction unit 310 is formed, for example, as a tubular member.

The suction unit 310 also may be configured to be movable by the vertical drive unit 311. The suction unit 310 is moved in the vertical direction by the controller 34 controlling the vertical drive unit 311. During washing, the suction unit 310 is lowered so that the tip 310a is disposed at a position corresponding to the exterior surface washer 332 (described later) of the first washing unit 330.

The first washing unit 330 is provided to wash the suction unit 310. The first washing unit 330 includes, for example, an interior surface washer 331 and an exterior surface washer 332.

The interior surface washer 331 is connected to a part on the opposite side of the tip 310a of the suction unit 310. The interior surface of the suction unit 310 is washed by a flow of washing liquid from the interior surface washer 331 to the interior of the suction unit 310.

The exterior surface washer 332 is disposed below the suction unit 310. The exterior surface washer 332 includes, for example, a washing liquid discharger 332a. The exterior surface of the suction unit 310 is washed by discharging washing liquid from the washing liquid discharger 332a toward the exterior surface of the suction unit 310. The exterior surface washer 332 also may be configured to drain the used waste liquid from a drainage part which is not shown in the drawing after the washing liquid is discharged and used from the interior surface washer 331 and washing liquid discharger 332*a*.

The dispensing unit 320 is provided to dispense the blood sample suctioned by the suction unit 310 onto a glass slide 500 (refer to FIG. 2) at the smear position. The dispensing unit 320 is formed, for example, as a tubular member.

The dispensing unit 320 also may be configured to be movable by the horizontal drive unit 321. The dispensing unit 320 is moved in the horizontal direction by the controller 34 controlling the horizontal drive unit 321. During washing, the dispensing unit 320 is moved to a position corresponding to an exterior surface washer 342 (described later) of the second washing unit 340.

The first second unit 340 is provided to wash the dispensing unit 320. The second washing unit 340 includes, for example, an interior surface washer 341 and an exterior surface washer 342.

The interior surface washer 341 is connected to a part on the opposite side of the tip 320*a* of the dispensing unit 320. The interior surface of the dispensing unit 320 is washed by a flow of washing liquid from the interior surface washer 341 to the interior surface of the dispensing unit 320.

The exterior surface washer 342 includes, for example, a washing liquid discharger 342*a*. The exterior surface of the dispensing unit 320 is washed by discharging washing liquid from the washing liquid discharger 342*a* toward the exterior surface of the dispensing unit 320. The exterior surface washer 342 also may be configured to be movable by the vertical drive unit 343. The exterior surface washer 342 is moved in the vertical direction by the controller 34 controlling the vertical drive unit 343. During washing, the exterior surface washer 342 is raised to the position of the tip 320*a* of the dispensing unit 320. The exterior surface washer 342 also may be configured to drain the used waste liquid from a drainage part which is not shown in the drawing after the washing liquid is discharged and used from the interior surface washer 341 and washing liquid discharger 342*a*.

Figure 4:
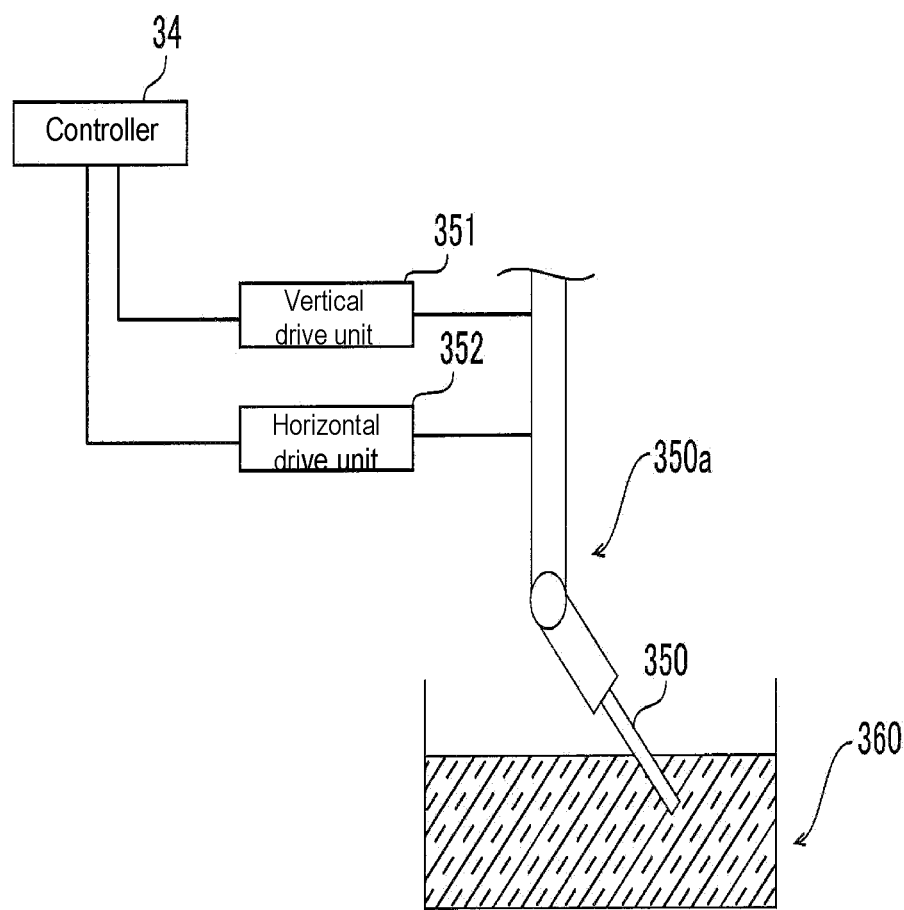
FIG. 4 is a schematic view showing the deployment member and third washing unit of the blood sample processing system of the embodiment.

As shown in FIG. 4, the smear preparation apparatus 30 and the blood processing unit 31 also may be provided with a deployment member 350. The washing unit 32 has a third washing unit 320. FIG. 4 shows the deployment member 350 as it is being washed by the third washing unit 360.

The deployment member 350 is provided to spread the blood sample dripped onto the glass slide 500 (refer to FIG. 2). The deployment member 350 is formed, for example, by a pull glass. The deployment member 350 is disposed at the tip of the support 350*a* of the deployment member 350. The operation of the deployment member 350 is controlled by the controller 34 so that the deployment condition for spreading the blood sample is changed to make the smear based on the hematocrit of the blood sample obtained from the blood cell analyzer 20 by the controller 34.

The support 350*a* of the deployment member 350 is connected to the vertical drive unit 351 and horizontal drive unit 352. The deployment member 350 is moved in the vertical direction and the horizontal direction by the controller 34 controlling the vertical drive unit 351 and horizontal drive unit 352. During washing, the deployment member 350 is lowered into the liquid accumulated in the third washing unit 360.

The third washing unit 360 is provided to wash the deployment member 350. The third washing unit 360, for example, performs ultrasonic washing of the deployment member 350 using the accumulated washing liquid. The third washing unit 360 is configured so that the washing liquid can be replaced after the washing of the deployment member 350 is completed.

The first washing unit 330, second washing unit 340, and third washing unit 360 are controlled by the controller 34 so that the washing operation is performed for a preset fixed time in the first washing operation.

Returning to FIG. 2, the controller 34 of the smear preparation apparatus 30, for example, is configured to obtain information related to the presence of abnormal blood cells, and controls the operation of the washing unit 32 to change the washing condition of the washing operation to be performed after processing of the blood sample based on the information related to the presence of abnormal blood cells. The controller 34, for example, also may obtain the washing condition change order information, and control the operation of the washing unit 32 to change the washing condition of the washing operation after processing a blood sample based on the washing condition change order information.

The controller 34 changes the washing condition under which the washing is performed after processing the blood sample to the second washing condition which is stronger than the first washing condition when the number of abnormal blood cells exceeds a predetermined threshold value. According to this configuration, the washing condition can be changed to the second washing condition which is stronger than the first washing condition by a simple control process.

The controller 34 changes the washing condition for washing to be performed after processing a blood sample to the second washing condition which is stronger than the first washing condition when the presence of abnormal blood cells in the blood sample is suggested. The controller 34 changes the washing condition for washing to be performed after processing a blood sample to the second washing condition which is stronger than the first washing condition based on the abnormal blood cell flag. Therefore, carryover of abnormal blood cells that might adversely affect the diagnosis when mildly present is effectively avoided, an increase in time required to prepare the smear is prevented while avoiding an increase in washing liquid reagent consumption.

The controller 34 changes the washing condition for washing to be performed after processing a blood sample to the second washing condition which is stronger than the first washing condition based on information related to abnormal white blood cells or abnormal red blood cells. For example, the controller 34 performs a process of washing the blood processing unit 31 by controlling the operation of the washing unit 32 to change the washing operation after processing the blood sample based on information related to abnormal white blood cells. Therefore, carryover of a blood sample containing abnormal white blood cells to the next smear can be prevented because the blood processing unit 31 is adequately washed by the washing unit 32 even when a smear has been prepared of a sample containing abnormal white blood cells that are not usually found in peripheral blood of healthy subjects. Note that the information related to abnormal white blood cells is one example of information related to the presence of abnormal blood cells used by the blood cell analyzer 20, and also may be, for example, information related to the number of abnormal white blood cells, or an abnormal blood cell flag based on the number of abnormal white blood cells.

Carryover of a blood sample containing abnormal red blood cells to the next smear also can be prevented the same as when a smear is prepared of a blood sample containing abnormal white blood cells because the controller 34 performs the process of washing the blood cell processing unit 31 to change the washing condition to the second washing condition which is stronger than the first washing condition based on information related to abnormal red blood cells even when a smear of abnormal red blood cells is prepared. The information related to abnormal red blood cells is one example of information related to the presence of abnormal blood cells used by the blood cell analyzer 20, and also may be, for example, information related to the number of abnormal red blood cells, or an abnormal blood cell flag based on the number of abnormal red blood cells.

The controller 34 can control the operation of the first washing unit 330 to change the washing condition for washing after processing a blood sample to the second washing condition which is stronger than the first washing condition when abnormal blood cells occur in the blood sample. The controller 34 is configured to control the operation of the operation of the first washing unit 330 to change the washing condition in the washing operation of the suction unit 310 by the first washing unit 330 based on information related to the presence of abnormal blood cells. For example, the controller 34 performs a process of washing the suction unit 310 by controlling the operation of the first washing unit 330 to change the washing condition of the washing operation after processing the blood sample based on information related to abnormal white blood cells. The controller 34 also is configured to control the operation of the first washing unit 330 to change the washing condition in the washing operation of the suction unit 310 by the first washing unit 330 based on washing condition change order information. Therefore, the suction unit 310 is adequately washed by the first washing unit 330 and carryover of abnormal white blood cells to the next smear is effectively prevented even when a smear has been prepared of a sample containing abnormal white blood cells that are usually not present in peripheral blood of healthy subjects.

The controller 34 can control the operation of the second washing unit 340 to change the washing condition for washing after processing a blood sample to the second washing condition which is stronger than the first washing condition when abnormal blood cells occur in the blood sample. The controller 34 is configured to control the operation of the operation of the second washing unit 340 to change the washing condition in the washing operation of the dispensing unit 320 by the second washing unit 340 based on information related to the presence of abnormal blood cells. For example, the controller 34 performs a process of washing the dispensing unit 320 by controlling the operation of the second washing unit 340 to change the washing condition of the washing operation after processing the blood sample based on information related to abnormal white blood cells. The controller 34 also may be configured to control the operation of the second washing unit 340 to change the washing condition in the washing operation of the dispensing unit 320 by the second washing unit 340 based on washing condition change order information. Therefore, the dispensing unit 320 is adequately washed by the second washing unit 340 and carryover of abnormal white blood cells to the next smear is effectively prevented even when a smear has been prepared of a sample containing abnormal white blood cells that are usually not present in peripheral blood of healthy subjects.

The controller 34 can control the operation of the third washing unit 360 to change the washing condition for washing after processing a blood sample to the second washing condition which is stronger than the first washing condition when abnormal blood cells occur in the blood sample. The controller 34 is configured to control the operation of the third washing unit 360 to change the washing condition in the washing operation of the deployment member 350 by the third washing unit 360 based on information related to the presence of abnormal blood cells. For example, the controller 34 performs a process of washing the deployment member 350 by controlling the operation of the third washing unit 360 to change the washing condition of the washing operation after processing the blood sample based on information related to abnormal white blood cells. The controller 34 also is configured to control the operation of the third washing unit 360 to change the washing condition in the washing operation of the deployment member 350 by the third washing unit 360 based on washing condition change order information. Therefore, the deployment member 350 is adequately washed by the third washing unit 360 and carryover of abnormal white blood cells to the next smear is effectively prevented even when a smear has been prepared of a sample containing abnormal white blood cells that are usually not present in peripheral blood of healthy subjects.

The controller 34 may also change the washing condition for washing to be performed after processing a blood sample to the second washing condition which is stronger than the first washing condition based on information related to immature blood cells as abnormal white blood cells. Therefore, carryover of a blood sample containing immature blood cells to the next smear can be effectively prevented even when a smear containing immature blood cells has been prepared.

The controller 34 may also change the washing condition for washing to be performed after processing a blood sample to the second washing condition which is stronger than the first washing condition based on information related to blast cells as abnormal white blood cells. Carryover of blast cells to the next smear can be effectively prevented even when a smear containing blast cells has been prepared.

The controller 34 also may control the operation of the washing unit 32 to change the washing condition of washing after processing a blood sample to the second washing condition which is stronger than the first washing condition based on information related to the number of red blood cells of white blood cells that are neither abnormal white blood cell nor abnormal red blood cells. Therefore, carryover of white blood cells or red blood cells from the previous blood sample to the next smear can be prevented because adequate washing operation are performed even when a smear has been prepared with an abnormal number of white blood cells or red blood cells the same as when a smear has been prepared with an abnormal white blood cells or abnormal red blood cells as described above.

The controller 34 also may control the operation of the washing unit 32 to change the washing condition of the washing operation performed after processing the blood sample based on at least one among the white blood cell count, red blood cell count, abnormal white blood cell count, or abnormal red blood cell count exceeding a corresponding threshold value. Therefore, the washing condition can be easily changed.

Obtaining Information by the Information Obtaining Unit

The information obtaining unit 33 of the smear preparation apparatus 30 also may obtain the washing condition change order information generated by blood cell analyzer 20. The information obtaining unit 33 also may obtain the washing condition change order information generated by the blood cell analyzer 20 from the blood cell analyzer 20 through the host computer 50. The controller 34 can change the washing condition to the second washing condition which is stronger than the first washing condition based on the washing condition change order information obtained by the information obtaining unit 33. Therefore, the control load of the controller 34 is reduced and adequate washing can be performed.

The information obtaining unit 33 also may obtain the information related to the presence of abnormal blood cells generated by the blood cell analyzer 20 from the blood cell analyzer 20 through the host computer 50. Therefore, the control load of the controller 34 is reduced and adequate washing can be performed.

The information obtaining unit 33 also may obtain the washing condition change order information generated by the host computer 50 from the host computer 50.

The information obtaining unit 33 also may obtain the preparation order information of the smear generated when the analyzer unit 70 of the blood cell analyzer 20 or the host computer 50 determines whether a smear will be prepared by the smear preparation apparatus 30, washing condition change order information, and information related to the presence of abnormal blood cells. Therefore, the information obtaining unit 33 simplifies the process of obtaining information more than when the smear preparation order information, washing condition change order information, and information related to the presence of abnormal blood cells are obtained separately.

The information obtaining unit 33 also may obtain the hematocrit of the blood sample, and information related to the presence of abnormal blood cells or washing condition change order information together from the blood cell analyzer 20. Therefore, the process of obtaining information is simplified more than when the controller 34 obtains the hematocrit of the blood sample, and the washing condition change order information or information related to the presence of abnormal blood cells separately.

The controller 34 is configured to control the operation of the washing unit 32 to change the washing condition of the washing operation to be performed after processing the blood sample to the second washing condition which is stronger than the first washing condition based on the washing condition change order information or information related to the presence of abnormal blood cells. Note that the washing liquid used in the first washing condition is water containing an antiseptic and surfactant. The washing liquid used in the first washing condition is substantially free of chlorine. In the first washing condition a single washing is performed using this washing liquid.

For example, the controller 34 controls the operation of the second washing unit 32 to change the washing condition for washing after processing a blood sample to the second washing condition which is stronger than the first washing condition so that the blood processing unit 31 is washed a plurality of times. Ideally, the controller 34 controls the operations of the first washing unit 330, second washing unit 340, and third washing unit 360 to perform the washing operation a plurality of times, and executes processes to respectively wash the suction unit 310, dispensing unit 320, and deployment member 350. The number of wash cycles in the second washing condition is greater than the number of wash cycles in the first washing condition, for example, two wash cycles. The number of wash cycles also may be three or more. Therefore, the suction unit 310, dispensing unit 320, and deployment member 350 can be adequately washed by the first washing unit 330, second washing unit 340, and third washing unit 360 by a simple method even when a smear containing abnormal white blood cells has been prepared, for example. As a result, carryover to the next smear is easily prevented.

Other Examples of Changing the Washing Condition

In the second washing condition, the method of washing under a stronger condition than the normal first washing condition may include various methods other than changing the number of wash cycles.

The controller 34 also may change the washing condition of the washing performed after processing the blood sample to the second washing condition which is stronger than the first washing condition so that washing is performed using a washing liquid containing chlorine which is different from the washing liquid used in the washing operation under the first washing condition. For example, the controller 34 also may control the operation of the first washing unit 330 and the second washing unit 340 to respectively wash the suction unit 310 and the dispensing unit 320 using the washing liquid that contains chlorine. The controller 34 also, for example, may perform a process to wash the suction unit 310 and dispensing unit 320 after suctioning and dispensing a blood sample containing abnormal white blood cells using the washing liquid that contains chlorine based on the washing condition change order information or information related to the presence of abnormal blood cells when a test tube accommodating the washing liquid containing chlorine is set in the urgent sample container part 300a of the smear preparation apparatus 30. The chlorine-containing washing liquid is suctioned by the suction unit 310 and dispensed by the dispensing unit 320. Therefore, the suction unit 310 and dispensing unit 320 can be reliably washed even when a smear of abnormal white blood cells has been prepared. As a result, carryover of the blood sample that includes abnormal white blood cells to the next smear can be easily prevented.

The controller 34 also may change the washing condition of the washing performed after processing the blood sample to the second washing condition which is stronger than the first washing condition so that the volume of the washing liquid is greater than the volume of the washing liquid used in the washing operation under the first washing condition. For example, the controller 34 also may perform processes to respectively wash the suction unit 310, dispensing unit 320, and deployment member 350 by the first washing unit 330, second washing unit 340, and third washing unit 360 using double the usual volume of washing liquid. Therefore, the suction unit 310, dispensing unit 320, and deployment member 350 can be reliably and adequately washed by the first washing unit 330, second washing unit 340, and third washing unit 360 even when a smear containing abnormal white blood cells has been prepared.

The controller 34 also may change the washing condition of the washing performed after processing the blood sample to the second washing condition which is stronger than the first washing condition so that the washing time is greater than the washing time used in the washing operation under the first washing condition. For example, the controller 34 also may perform processes to respectively wash the suction unit 310, dispensing unit 320, and deployment member 350 by the first washing unit 330, second washing unit 340, and third washing unit 360 using double the usual washing time. Therefore, the suction unit 310, dispensing unit 320, and deployment member 350 can be reliably and adequately washed by the first washing unit 330, second washing unit 340, and third washing unit 360 even when a smear containing abnormal white blood cells has been prepared.

The degree of strength also may be changed when the washing condition is made stronger than the usual washing condition.

Specifically, the controller 34 also may change the washing condition of the washing performed after processing the blood sample to the second washing condition which is stronger than the first washing condition to change the degree of washing strength in the washing operation of the second washing condition when abnormal blood cells are present in the blood sample. For example, the controller 34 also may control the operation of the washing unit 32 to change the washing condition of the washing operation to change the degree of washing strength in the washing operation under the second washing condition based on information related to the presence of abnormal blood cells. The controller 34 also may control the washing operation so that washing is performed for two wash cycles when the abnormal white blood cell count exceeds a first threshold value, and washing is performed for three wash cycles when the abnormal white blood cell count exceeds a second threshold value based on a plurality of threshold values such as a first threshold and second threshold related to the abnormal white blood cell count, for example. The controller 34 also may control the washing operation based on a plurality of threshold values related to the white blood cell count, red blood cell count, and abnormal red blood cell count just as in the case of abnormal white blood cells.

When abnormal blood cells are present in a blood sample, the abnormal blood cell flag can be generated by the controller 74 of the analyzing unit 70 or the controller 53 of the host computer 50 to change the degree of washing strength in the washing operation performed under the second washing condition. When abnormal blood cells are present in a blood sample, the washing condition change order information also can be generated by the controller 74 of the analyzing unit 70 or the controller 53 of the host computer 50 to change the degree of washing strength in the washing operation performed under the second washing condition.

The controller 34 controls the operation of the washing unit 32 to perform the washing operation after each blood sample processing operation. The controller 34 controls the respective first washing unit 330, second washing unit 340, and third washing unit 360 to wash the suction unit 310, dispensing unit 320, and deployment member 350 after the blood sample suctioned by the suction unit 310 is dripped on the glass slide 500 by the dispensing unit 320 and the deployment member 350 has spread the dripped blood sample on the glass slide 500. Therefore, carryover to the next smear is prevented because the washing operation is performed before preparing the next smear even when a smear of abnormal blood cells has been prepared.

Other System Structures

Figure 5:
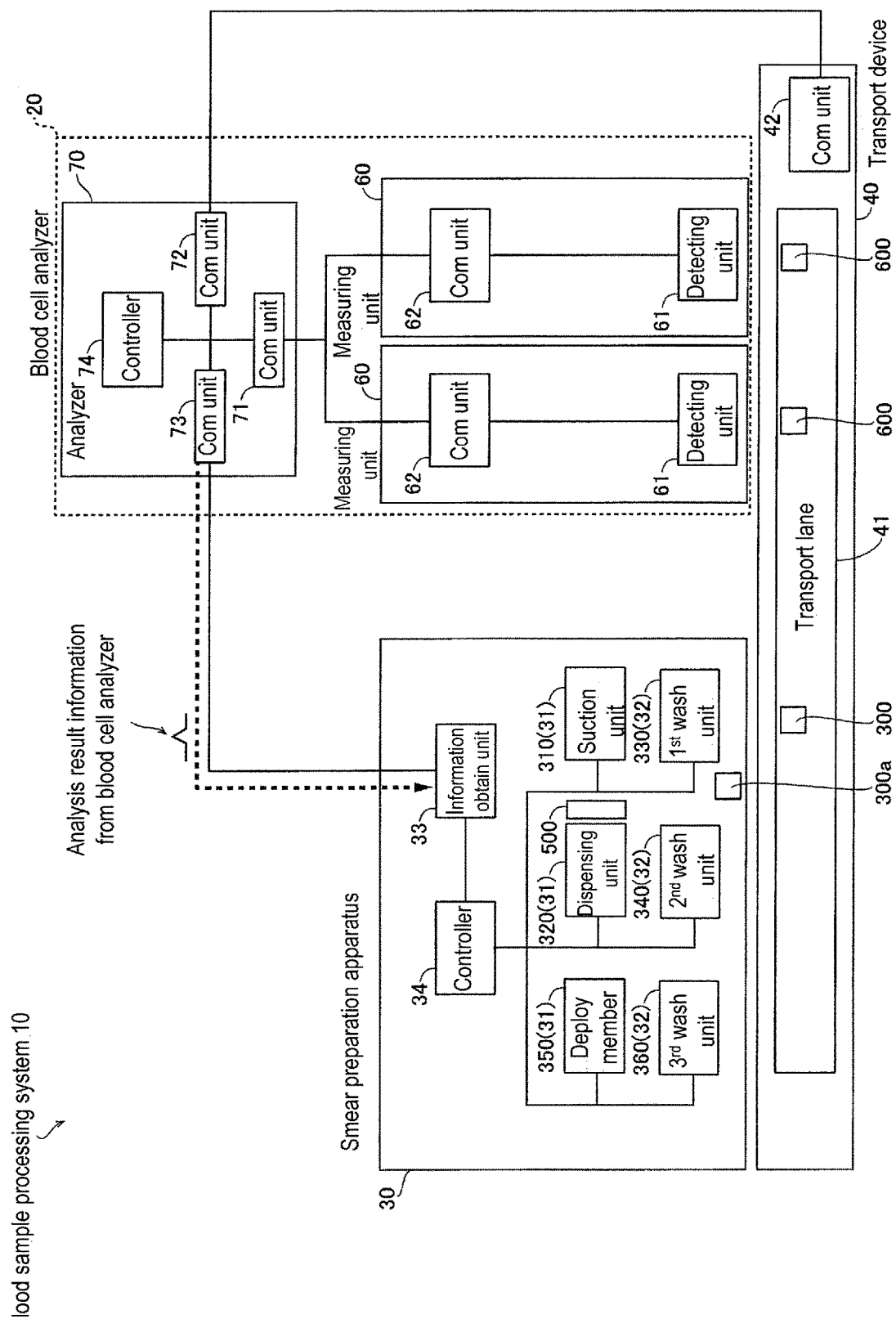
FIG. 5 is a block diagram of another example of the embodiment of the blood sample processing system.

Although the example shows the blood sample processing system 10 provided with a blood cell analyzer 20, smear preparation apparatus 30, transporting device 40, ands host computer 50, the configuration of the blood sample processing system 30 may be modified as appropriate. Although the blood sample processing system 10 includes the blood cell analyzer 20, smear preparation apparatus 30, and transporting device 40, the system also, for example, may omit the host computer 50 as shown in FIG. 5. In this case the analyzing unit 70 of the blood cell analyzer 20 is configured to create a direct measurement order.

Figure 6:
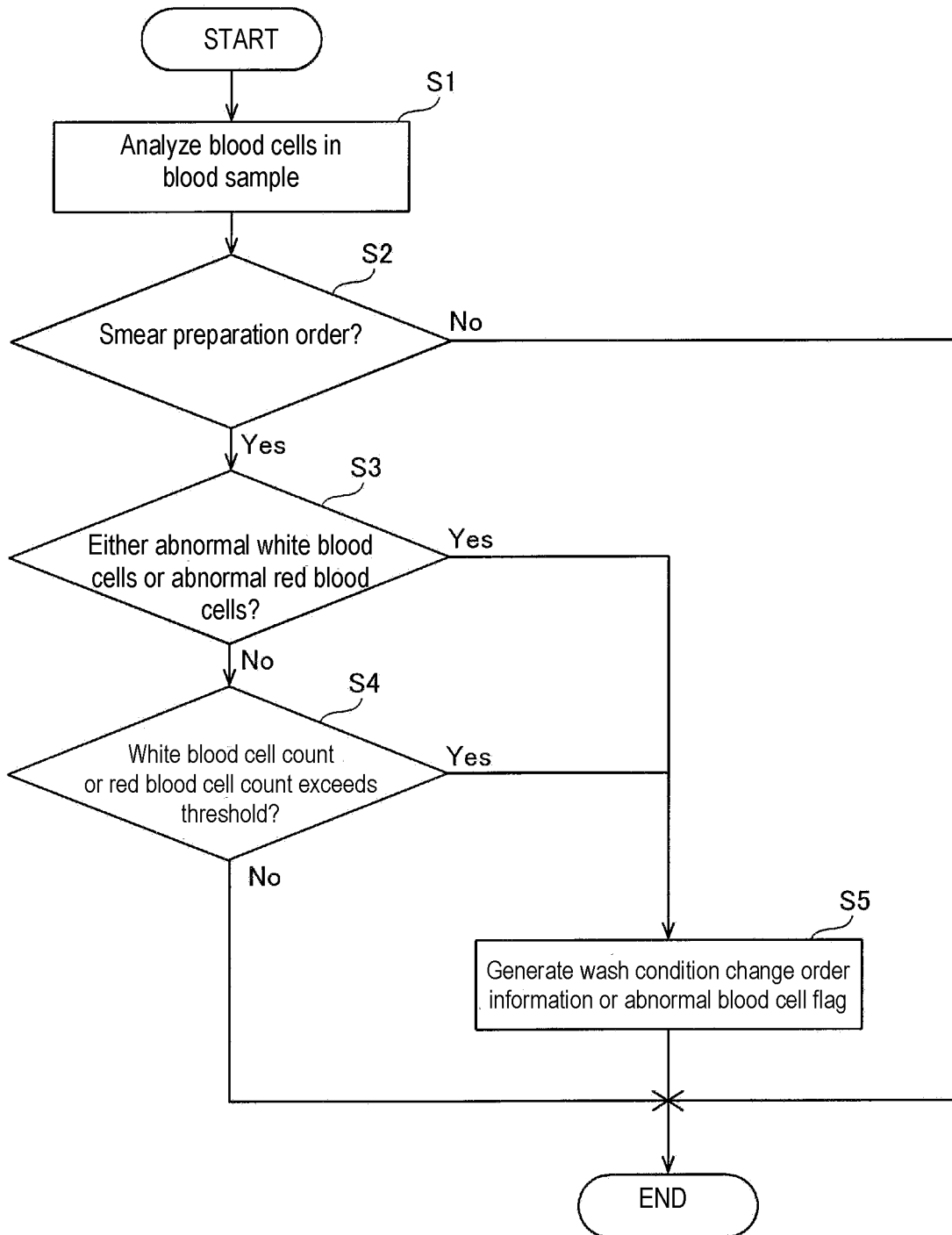
FIG. 6 is a flow chart describing the generation process of the washing condition change order information or the abnormal cell flag.

Washing Condition Change Order Information or Abnormal Blood Cell Flag Generation Process The process of generating the washing condition change order information or abnormal blood cell flag by the controller 74 of the analyzing unit 70 is described below with reference to FIG. 6. This process is described below by way of example implemented by the controller 74 of the analyzing unit 70.

In step S1, the controller 74 executes a process to analyze the blood cells in the blood sample in the blood cell analyzer 20. Specifically, the controller 74 queries the host computer 50 for a sample measurement order when a bar-code reader (not shown in the drawing) of the measuring unit 60 reads the ID of a test tube that has been moved to the suction process position 600. The controller 74 then controls the measurement operation of the measuring unit 60 based on the measurement order received from the host computer 50. The controller 74 obtains information related to the blood cell count for determining the presence of abnormal blood cells from the blood cell analyzer 20 based on the measurement results obtained by the measuring unit 60.

In step S2, the controller 74 determines whether there is an order to prepare a smear. The controller 74 determines the necessity of preparing a smear based on the analysis results of the blood sample, and issues the order. The controller 74 advances the process to step S3 when there is an order to prepare a smear. On the other hand, the controller 74 ends the process of generating the washing condition change order information or the abnormal cell flag when there is no order to prepare a smear.

In step S3, the controller 74 determines whether at least one or the other of abnormal white blood cells or abnormal red blood cells are present. The controller 74 advances the process to step S5 when at least one or the other of abnormal white blood cells or abnormal red blood cells are present. On the other hand, the controller 74 advances the process to step S4 when neither abnormal white blood cells or abnormal red blood cells are present.

When the process advances to step S4, the controller 74 determines whether at least one or the other of the white blood cell count or red blood cell count is greater than a threshold value corresponding to the white blood cell count or red blood cell count. The controller 74 advances the process to step S5 when at least one or the other of the white blood cell count or red blood cell count is greater than the corresponding threshold value. On the other hand, the controller 74 ends the washing condition change order information generation process when both the white blood cell count and the red blood cell count are equal to or less than the corresponding threshold value.

When the process advances to step S5, the controller 74 generates the washing condition change order information to change the washing condition to strengthen the washing operation performed by the washing unit 32. The controller 74 also may generate the abnormal blood cell flag to change the washing condition to strengthen the washing operation performed by the washing unit 32. Thereafter, the controller 74 ends the process for generating the washing condition change order information or abnormal blood cell flag.

The washing condition change order information or abnormal blood cell flag are generated by the process described above. The controller 74 performs the process for generation the washing condition change order information or abnormal blood cell flag for every blood sample.

Washing Condition Change Process

Figure 7:
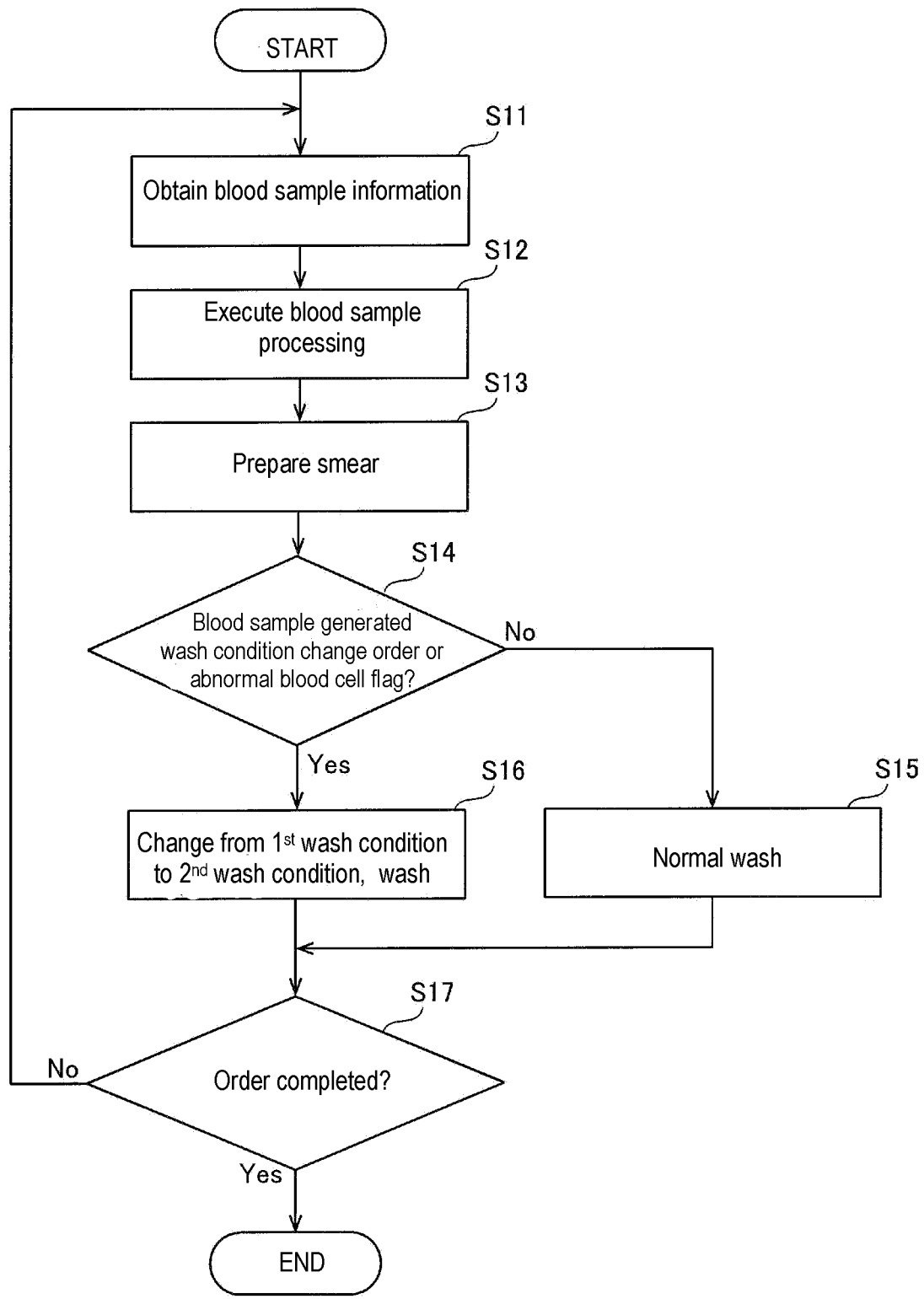
FIG. 7 is a flow chart describing the washing condition change process.

The Process for changing the washing condition performed by the controller 34 of the smear preparation apparatus 30 is described below with reference to FIG. 7.

In step S11, the controller 34 obtains the information of the blood sample being transported to the smear preparation apparatus 30. Specifically, the controller 34 obtains hematocrit information and the like of the blood sample, smear preparation order information, and washing condition change order information or abnormal blood cell flag generated in step S5 (refer to FIG. 6) of the process for generating the washing condition change order information or abnormal blood cell flag from the analyzing unit 70 of the blood cell analyzer 2.

In step S12, the controller 34 executes the processing of the blood sample. Specifically, the controller 34 executes the process to have the suction unit 310 suction the blood sample from the test tube transported to the suction process position 300 of the smear preparation apparatus 30. The controller 34 then executes the process to discharge the suctioned blood sample from the dispensing unit 320 onto the glass slide 500. The controller 34 then executes the process to have the deployment member 350 spread the dripped blood sample on the glass slide 500.

In step S13, the controller 34 executes the process to prepare the smear using the glass slide 500 (refer to FIG. 2) on which the blood sample was dripped in step S12.

In step S14, the controller 34 determines whether the blood sample has generated a washing condition change order information or an abnormal blood cell flag. The controller 34 advances the process to step S15 when the blood sample has not generated a washing condition change order information or an abnormal blood cell flag. On the other hand, the controller 34 advances the process to step S16 when the blood sample has generated a washing condition change order information or an abnormal blood cell flag.

The controller 34 executes normal washing when the process advances to step S15. Specifically, the controller 34 executes one wash cycle respectively for the suction unit 310, dispensing unit 320, and deployment member 350 through the first washing unit 330, second washing unit 340, and third washing unit 360 using water containing an antiseptic and surfactant under the first washing condition. Thereafter, the controller 34 advances the process to step S17.

When the process advances to step S16, the controller 34 changes the washing condition from the first washing condition to the second washing condition, and executes washing under the second washing condition. Specifically, the controller 34 executes the washing operation for two wash cycles respectively for the suction unit 310, dispensing unit 320, and deployment member 350 through the first washing unit 330, second washing unit 340, and third washing unit 360 using water containing an antiseptic and surfactant under the first washing condition. Thereafter, the controller 34 advances the process to step S17.

In step S17, the controller 34 determines whether the order to prepare a smear is completed. The controller 34 returns the process to step S11 when the order to prepare a smear has been completed. On the other hand, the controller 34 ends the washing condition change process when the order to prepare a smear has been completed.

The washing condition change process is performed by the processes described above. The controller 34 executes the washing condition change process for each blood sample.

Note that the present embodiments in all respects are examples and not to be regarded as limiting in any way. The scope of the invention is defined solely by the scope of the claims and not by the forgoing description, and may be variously and appropriately modified insofar as such modification is within the scope of the meaning expressed in the claims.

What is claimed is:

1. A smear preparation apparatus comprising:
   a blood processing device comprising a tubular member to suck a blood sample from a test tube and a smearing device to smear the blood sample on a glass slide;
   a washing device comprising a washing liquid conduit and a liquid dispenser configured to wash interior and exterior surfaces of the tubular member in the blood processing device under a first washing condition after the processing of the blood sample;
   at least one controller executes program code stored in a non-transitory memory to control operations of the blood processing device and the washing device; and
   an information obtaining device comprising a communication interface coupled to a blood cell analyzer configured to obtain information regarding blood cells in the blood sample;
   wherein the at least one controller is configured to;
   determine an occurrence of immature white blood cells in the blood sample based on the information regarding blood cells in the blood sample received by the information obtaining device, and
   in response to determining the occurrence of immature white blood cells in the blood sample, control the washing device to change the first washing condition to a second washing condition to be washed by the washing device, wherein the second washing condition is stronger than the first washing condition, wherein a stronger washing condition includes using at least one or a combination of: a washing liquid of high strength, higher number of wash cycles, longer washing cycles and larger volume of washing liquid.

2. The smear preparation apparatus of claim 1, wherein the at least one controller is configured to change the first washing condition after processing the blood sample to the second washing condition which is stronger than the first washing condition based on the determination of the occurrence of immature white blood cells in the blood sample.

3. The smear preparation apparatus of claim 1, wherein the at least one controller is configured to control the washing device to change the first washing condition to the second washing condition which is stronger than the first washing condition based further on information related to blast cells.

4. The smear preparation apparatus of claim 1, wherein the at least one controller is configured to control the washing device to change the first washing condition to the second washing condition which is stronger than the first washing condition based further on information related to the number of white blood cells or the number of red blood cells.

5. The smear preparation apparatus of claim 1, wherein the at least one controller is configured to control the washing device to change the first washing condition to the second washing condition which is stronger than the first washing condition based further on a determination that a number of abnormal blood cells exceeds a predetermined threshold value.

6. The smear preparation apparatus of claim 1, wherein the at least one controller is configured to control the washing device to change the first washing condition to the second washing condition which is stronger than the first washing condition when based further on a determination that the information regarding blood cells in the blood sample suggests the presence of abnormal blood cells.

7. The smear preparation apparatus of claim 1, wherein the at least one controller is further configured to control a preparation of a smear of the blood sample based on a hematocrit value of the blood sample obtained by the information obtaining device; and
the information obtaining device is configured to obtain information of the hematocrit value of the blood sample.

8. The smear preparation apparatus of claim 1, wherein the at least one controller is configured to control the washing device to change the first washing condition to the second washing condition which is stronger than the first washing condition to wash the blood processing unit a plurality of times.

9. The smear preparation apparatus of claim 1, wherein the at least one controller is configured to control the washing device to change the first washing condition to the second washing condition which is stronger than the first washing condition to perform the washing using a second washing liquid containing chlorine which is different from a first washing liquid used in the washing operation under the first washing condition.

10. The smear preparation apparatus of claim 1, wherein the at least one controller is configured to control the washing device to change the first washing condition to the second washing condition which is stronger than the first washing condition to change a level of washing strength of the washing operation under the second washing condition.

11. The smear preparation apparatus of claim 1, wherein the at least one controller is configured to control the washing device to change the first washing condition to the second washing condition which is stronger than the first washing condition to increase the amount of washing liquid in the washing operation under the first washing condition.

12. The smear preparation apparatus of claim 1, wherein the at least one controller is configured to control the washing device to perform a washing operation for every processing operation of a blood sample.

13. The smear preparation apparatus of claim 1, wherein the information obtaining device is further configured to obtain the information regarding blood cells in the blood sample from the blood cell analyzer which analyzes blood cells in the blood sample.

14. The smear preparation apparatus of claim 1, wherein the information obtaining unit is configured to obtain the information regarding blood cells in the blood sample from a host computer that manages the progress of the blood cell analyzing device which analyzes blood cells in the blood sample.

15. The smear preparation apparatus of claim 1, wherein the blood processing unit comprises a suction unit which suctions the blood sample; and
the washing unit comprises a first washing unit which washes the suction unit.

16. The smear preparation apparatus of claim 1, wherein the blood processing device comprises a deployment member which smears the dripped blood sample on a glass slide;
the washing device comprises an additional washing device which washes the deployment member; and
the at least one controller is further configured to control the operation of the additional washing device to change the washing condition for washing the deployment member after processing a blood sample to a fourth washing condition which is stronger than a third washing condition in response to determining the occurrence of immature white blood cells in the blood sample.

17. A blood sample processing system comprising:
the blood cell analyzer configured to analyze blood cells in the blood sample; and
the smear preparation apparatus of claim 1.

18. A method of washing a blood processing unit of a smear preparation apparatus comprising, the method comprising:
providing a smear preparation apparatus of claim 1;
a blood processing device comprising a tubular member, to prepare a smear of a blood sample from an external source by sucking the blood sample from a test tube and dispensing the blood sample onto a glass slide, and a smearing device to smear the blood sample on a glass slide, and a washing device comprising a washing liquid conduits and a liquid dispenser coupled to the tubular member to wash interior and exterior surfaces of the tubular members in the blood processing device under a first washing condition after processing the blood sample, the method comprising:
sucking, by the blood processing device, the blood sample from the test tube;
smearing, by the smearing device, the blood sample on the glass slide;
obtaining, by the information obtaining device, information regarding blood cells in the blood sample;
determining, by the at least one controller, the occurrence of immature white blood cells in the blood sample based on the information regarding blood cells in the blood sample received by the information obtaining device;
controlling, by the at least one controller, in response to determining the occurrence of immature white blood cells in the blood sample, the washing device to change the first washing condition to the second washing condition that is stronger than the first washing condition.

19. The smear preparation apparatus of claim 1, wherein the second washing condition is stronger than the first washing condition with respect to washing both the interior and exterior surfaces of the tubular member.

* * * * *